(12) United States Patent
Danias et al.

(10) Patent No.: US 10,946,076 B2
(45) Date of Patent: Mar. 16, 2021

(54) GLAUCOMA TREATMENT

(71) Applicants: THE RESEARCH FOUNDATION FOR THE STATE UNIVERSITY OF NEW YORK, Albany, NY (US); ICAHN SCHOOL OF MEDICINE AT MOUNT SINAI, New York, NY (US)

(72) Inventors: Ioannis Danias, Staten Island, NY (US); Oscar A. Candia, New Rochelle, NY (US); Rosana Gerometta, Corrientes (AR)

(73) Assignees: The Research Foundation for The State University of New York, Albany, NY (US); Icahn School of Medicine at Mount Sinai, New York, NY (US)

( * ) Notice: Subject to any disclaimer, the term of this patent is extended or adjusted under 35 U.S.C. 154(b) by 49 days.

(21) Appl. No.: 14/766,854

(22) PCT Filed: Feb. 12, 2014

(86) PCT No.: PCT/US2014/016020
§ 371 (c)(1),
(2) Date: Aug. 10, 2015

(87) PCT Pub. No.: WO2014/126997
PCT Pub. Date: Aug. 21, 2014

(65) Prior Publication Data
US 2015/0366953 A1 Dec. 24, 2015

Related U.S. Application Data

(60) Provisional application No. 61/764,256, filed on Feb. 13, 2013.

(51) Int. Cl.
| | | |
|---|---|---|
| *A61K 38/49* | (2006.01) | |
| *A61K 38/20* | (2006.01) | |
| *C12N 15/86* | (2006.01) | |
| *A61K 31/12* | (2006.01) | |
| *A61K 31/09* | (2006.01) | |
| *A61K 31/366* | (2006.01) | |
| *A61K 31/427* | (2006.01) | |
| *A61K 31/7088* | (2006.01) | |
| *C12N 7/00* | (2006.01) | |
| *A61K 48/00* | (2006.01) | |

(52) U.S. Cl.
CPC .............. *A61K 38/49* (2013.01); *A61K 31/09* (2013.01); *A61K 31/12* (2013.01); *A61K 31/366* (2013.01); *A61K 31/427* (2013.01); *A61K 31/7088* (2013.01); *A61K 38/204* (2013.01); *C12N 7/00* (2013.01); *C12N 15/86* (2013.01); *A61K 48/00* (2013.01); *C12N 2710/10341* (2013.01); *C12N 2740/15043* (2013.01); *C12N 2740/15071* (2013.01); *C12N 2750/00043* (2013.01); *C12N 2750/00071* (2013.01); *C12Y 304/21068* (2013.01)

(58) Field of Classification Search
CPC .................. A61K 38/49; C12Y 304/21068
See application file for complete search history.

(56) References Cited

U.S. PATENT DOCUMENTS

2009/0202524 A1* 8/2009 Fleenor .................. A61K 31/19
424/130.1

FOREIGN PATENT DOCUMENTS

| RU | 2416402 C1 | 4/2011 |
|---|---|---|
| WO | WO 2008/055205 A2 | 5/2008 |

OTHER PUBLICATIONS

Zalta et al. "Intracameral Tissue Plasminogen Activator Use in a Large Series of Eyes With Valved Glaucoma Drainage Implants" Arch Ophthalmol/vol. 120, 1487-1493 Nov. 2002.*
Kwan et al. "A Study of Retinal Penetration of Intravitreal Tenecteplase in Pigs" Investigative Ophthalmology & Visual Science, Jun. 2006, vol. 47, No. 6.*
International Search Report and Written Opinion dated May 22, 2014 issued in PCT/US2014/016020.

* cited by examiner

*Primary Examiner* — Heidi Reese
(74) *Attorney, Agent, or Firm* — Scully, Scott, Murphy & Presser, P.C.

(57) ABSTRACT

Disclosed herein are methods of treatment for an intraocular pressure (IOP)-associated condition in a subject, that include administering to the subject an effective amount of a tissue plasminogen activator (tPA) therapeutic agent. In one embodiment, the IOP-associated condition is glaucoma. The administration of a tPA therapeutic agent can be an extended administration intended to cause a reduction in IOP in the subject for a period of at least one day to a year or more, relative to IOP levels in the subject prior to administration of the tPA therapeutic agent. The tPA therapeutic agent can be, for example, tPA, a tPA derivative, a small molecule direct or indirect tPA agonist, or a gene therapy vector.

18 Claims, 13 Drawing Sheets

GLAUCOMA TREATMENT

CROSS REFERENCE TO RELATED APPLICATION

This application is related to and claims the benefit of U.S. Provisional Patent Application No. 61/764,256 filed Feb. 13, 2013, the entire contents of which are incorporated by reference herein.

STATEMENT REGARDING FEDERALLY SPONSORED RESEARCH OR DEVELOPMENT

This invention was made with government support under Contract No. NEI EY020670 awarded by the National Institutes of Health/National Eye Institute. The government has certain rights in the invention.

BACKGROUND OF THE DISCLOSURE

The fibrinolytic system is a complex system of proteins that controls clotting of blood and subsequent dissolution of the resulting thrombus. Tissue plasminogen activator (tPA) and urokinase-type plasminogen activator (uPA, also known simply as urokinase) are two serine kinases that activate plasminogen by proteolytic cleavage. Activated plasminogen becomes plasmin with the ability to degrade fibrin. tPA also has activity at the cellular level for controlling ECM remodeling and has been implicated in cell proliferation and migration.

tPA activation is controlled by endogenous inhibitors, plasminogen activator inhibitors 1 (PAI1) and 2 (PAI2). PAI1 has been reported to be elevated in glaucoma in the past (Dan, J., et al., *Arch Ophthalmol* 123(2):220-4 (2005)) and has been shown to be synthesized by both the ciliary epithelium (Meyer, M. W., et al, *Graefes Arch Clin Exp Ophthalmol* 240(8):679-86 (2002)) and trabecular meshwork (TM) cells in response to TGF-β (Fuchshofer, R., et al., *Exp Eye Res* 77(6):757-65 (2003), Fleenor, D. L., et al., *Invest Ophthalmol Vis Sci* 47(1):226-34 (2006)), a known factor that induces reduction in outflow facility. tPA has also been reported to be down regulated in organ cultures after treatment with steroids (Snyder, R. W., et al., *Exp Eye Res* 57(4):461-8 (1993), Seftor, R. E., et al., *J Glaucoma* 3(4): 323-8 (1994)). It appears that some of the effects of PAI are mediated through activation of matrix metalloproteinases (MMPs) in the T M (Fuchshofer, R., et al., *Exp Eye Res* 77(6):757-65 (2003)).

Recombinant human tPA (rh-tPA or h-tPA) has been used for the acute management of excessive fibrin in the anterior segment of the eye, and for the dissolution of subretinal hemorrhages. Common off-label use of tPA is for treatment of acute fibrin build-up in the immediate post-operative period following glaucoma surgery. Although short-term IOP reductions have been mentioned following treatment with tPA, they have been attributed to the dissolution of the fibrin clot in the anterior chamber. Accordingly, longer-term treatment with tPA, or administration of tPA in the absence of fibrin build-up, has not been suggested in the prior art. Long-term tPA administration is not recommended in the art for several reasons, for example, to avoid a risk of excessive ocular bleeding/hemorrhage.

To date no attempt has been made to use tPA for therapeutic purposes in steroid induced glaucoma or other forms of glaucoma.

BRIEF SUMMARY OF THE DISCLOSURE

Disclosed herein are methods of treatment for an intraocular pressure (IOP)-associated condition in a subject, that include administering to the subject an effective amount of a tissue plasminogen activator (tPA) therapeutic agent. In one embodiment, the IOP-associated condition is glaucoma. In one embodiment, an effective amount is an amount in the range of 10-120 µl.

In contrast to prior art uses of tPA for short-term or acute treatment, tPA therapeutic agents are disclosed herein as beneficial under conditions of extended or recurrent administration. The recurrent administration of the tPA therapeutic agent over an extended period of time, such as at least two weeks, at least one month, at least six months, or a year or more, can cause a reduction in IOP in the subject for a period of at least two weeks to a year or more, relative to IOP levels in said subject prior to administration of the tPA therapeutic agent.

The tPA therapeutic agent can be, for example, tPA; a tPA variant, functional derivative, or homolog; a small molecule tPA agonist; an RNA molecule that causes tPA upregulation; a polypeptide or other molecule that causes tPA upregulation; an RNA molecule or other agent that down-regulates a negative regulator of tPA expression or activity; and a gene therapy vector. The tPA gene therapy vector can be a lentivirus or adeno-associated virus (AAV)-based vector encoding a tPA gene or a tPA derivative gene. The tPA gene therapy vector can contain a nucleic acid sequence encoding tPA; encoding a tPA functional derivative or homolog; encoding a polypeptide or other molecule that causes up-regulation of tPA expression; or encoding a polypeptide or other molecule that causes down-regulation of a negative regulator of tPA expression.

In one embodiment, the tPA therapeutic agent is a small molecule tPA agonist, or an analog of a small molecule tPA agonist, the small molecule tPA agonist being selected from the group consisting of: an oxysterol, N-acetyl-cysteine, Neovastat, nicotine, allopregnanolone, testosterone, forskolin, L-threo-DOPS, PACAP, a PDE4 activator, 5-azacytidine, CPT-cAMP, retinoic acid, a phorbol ester, 8-bromo-cAMP, 2-diocynoyl-sn-glycerol (diC8), Phorbol 12 myristate 13 acetate (PMA), AF12198, CE3F4, Prostaglandin E2 (PGE2), Butyrate, 1,25-dihydroxyvitamin D-3, estradiol, an estrogen analogue, laminin, Interleukin-6 (IL-6), ascorbic acid, sesamol, and lysophosphatidylcholine. The tPA therapeutic agent can be administered by various methods, such as by intraocular injection.

The tPA therapeutic agent can be administered, for example, topically, systemically, by injection, by iontophoresis, or by implantation of cells that produce said tPA therapeutic agent.

only. TA+AdPLAT, average outflow facility of eyes treated with TA and transfected with AdPLAT vector, showing expression of mCherry/AdPLAT. TA+/−AdPLAT, average outflow facility of eyes treated with TA and transfected with AdPLAT vector, showing no or minimal expression of mCherry/AdPLAT.

Figure 2A:
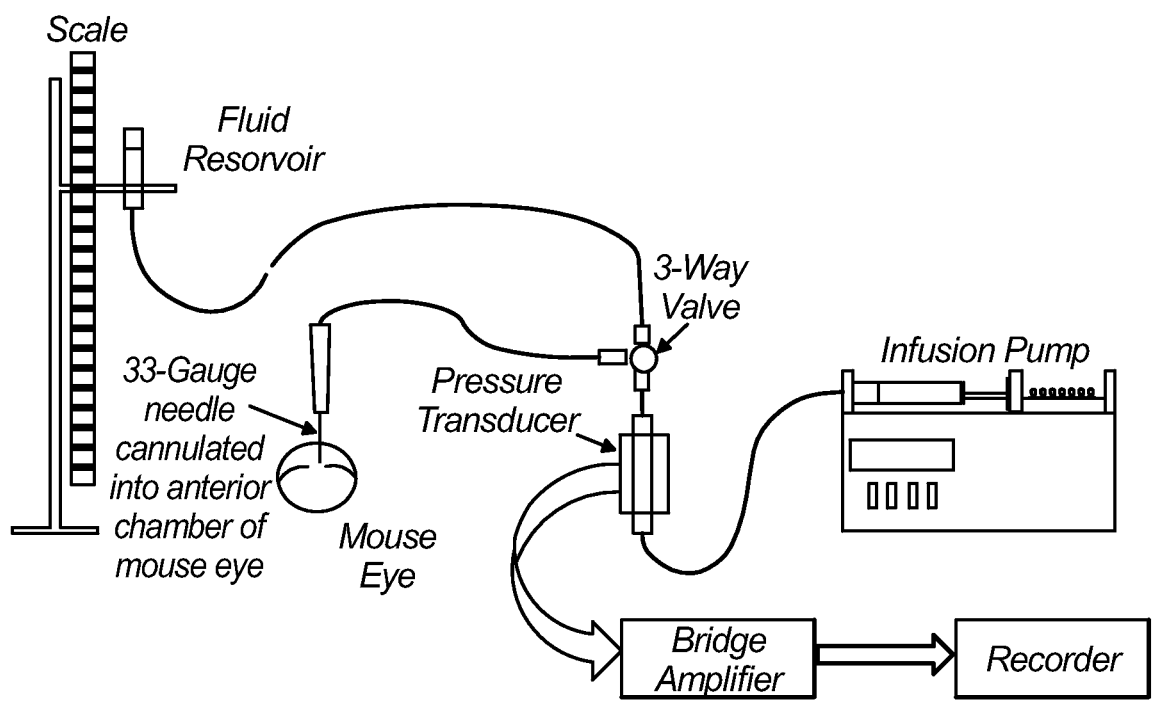
Figure 2B:
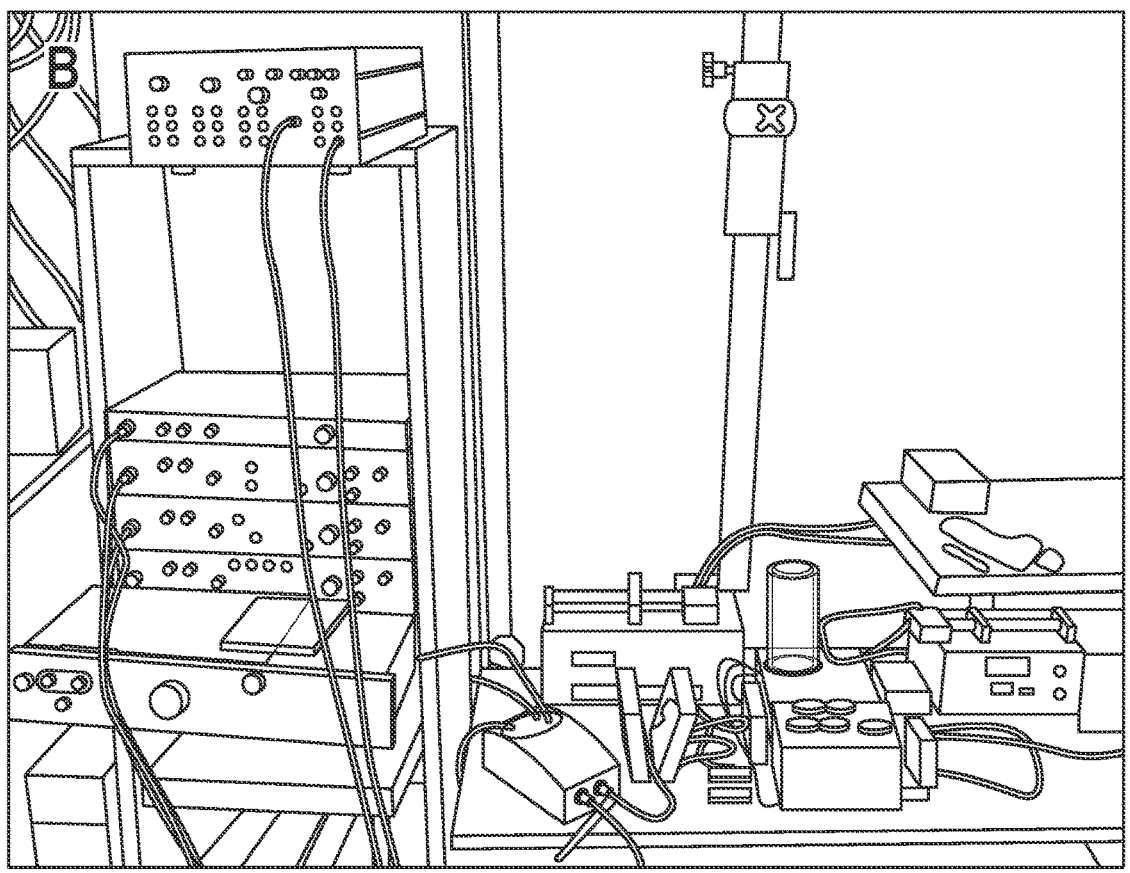
Figure 2C:
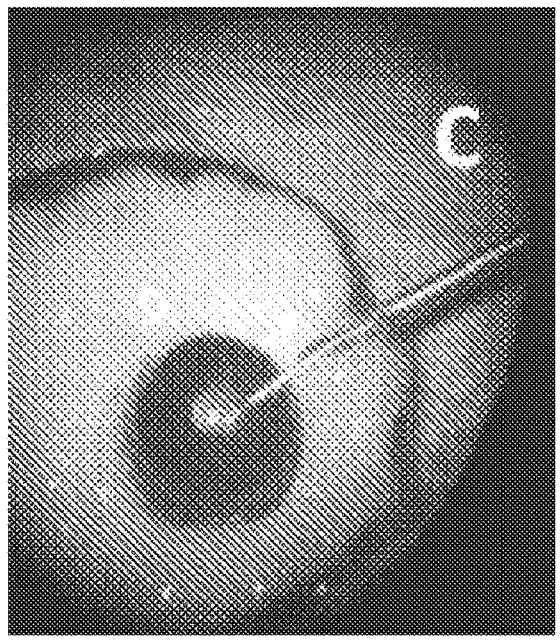

FIGS. 2A-2C. Device and method to measure outflow facility. (A), schematic for device used to measure outflow facility. (B), outflow facility measuring device, which includes a three-way valve which is connected to (i) a cannula for insertion into the eye; (ii) a flow-through pressure transducer; and (iii) a fluid reservoir. The pressure transducer is connected to a syringe loaded into a microdialysis infusion pump. For continuous pressure recording, the pressure transducer is attached to a bridge amplifier and the signal is fed into a chart or digital recorder. (C), eye is cannulated with a custom-made 33-gauge needle and connected via short PE60 tubing to the three-way valve.

Figure 3:
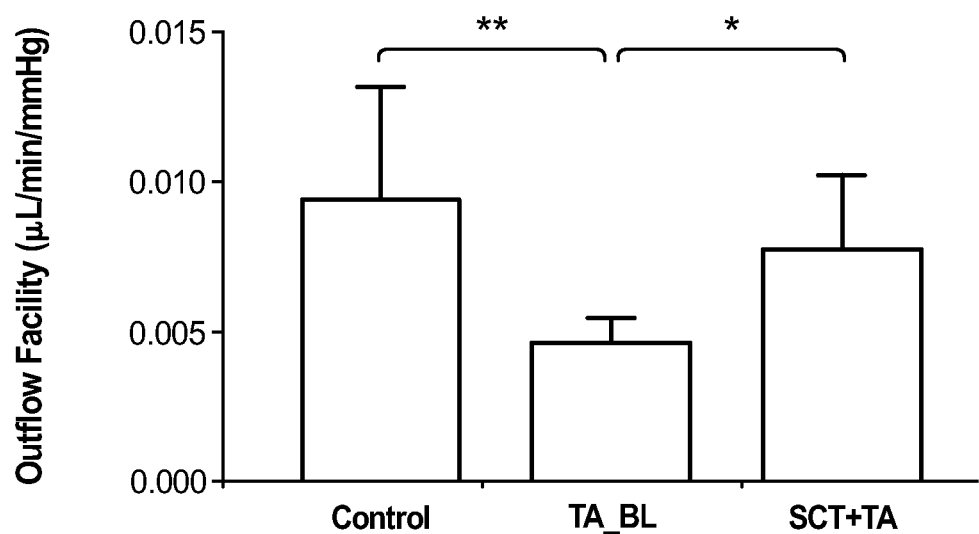

FIG. 3. Effect of SCT (simvastatin, curcumin and troglitazone) mixture on outflow facility (μl/min/mmHg) after 1 week of TA injection. SCT administration improves outflow facility in treated eye of mice.

Figure 4A:
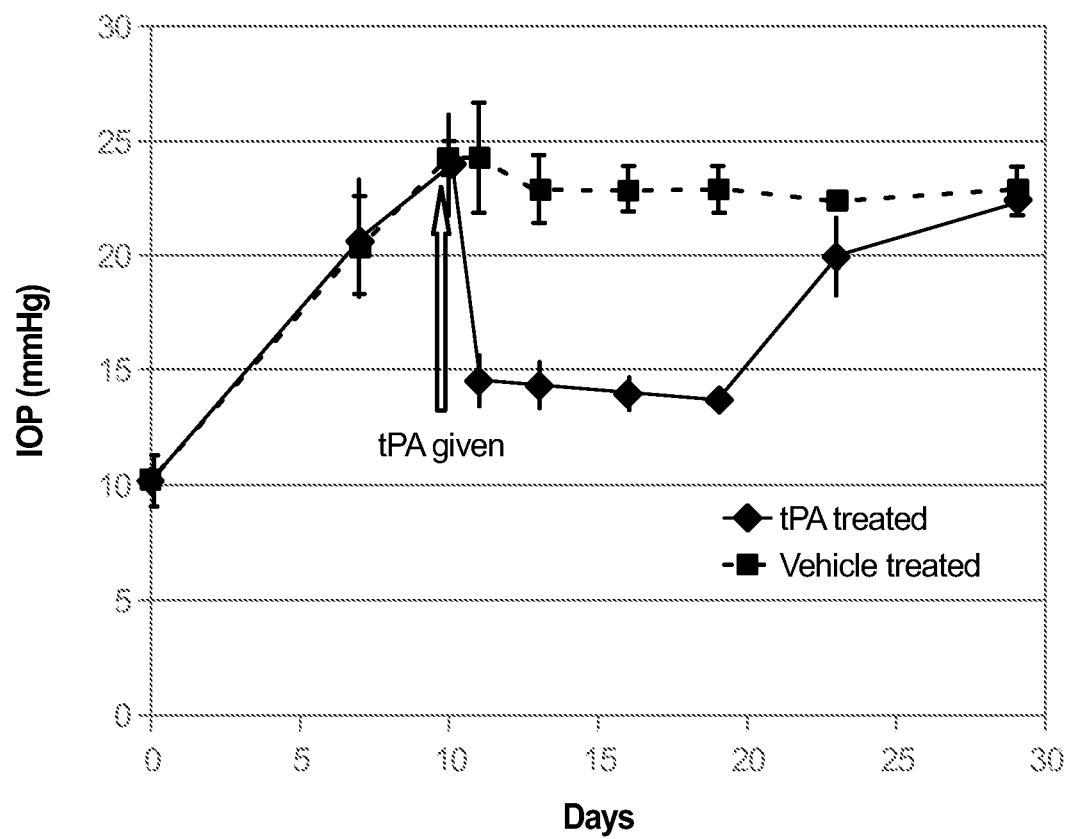
Figure 4B:
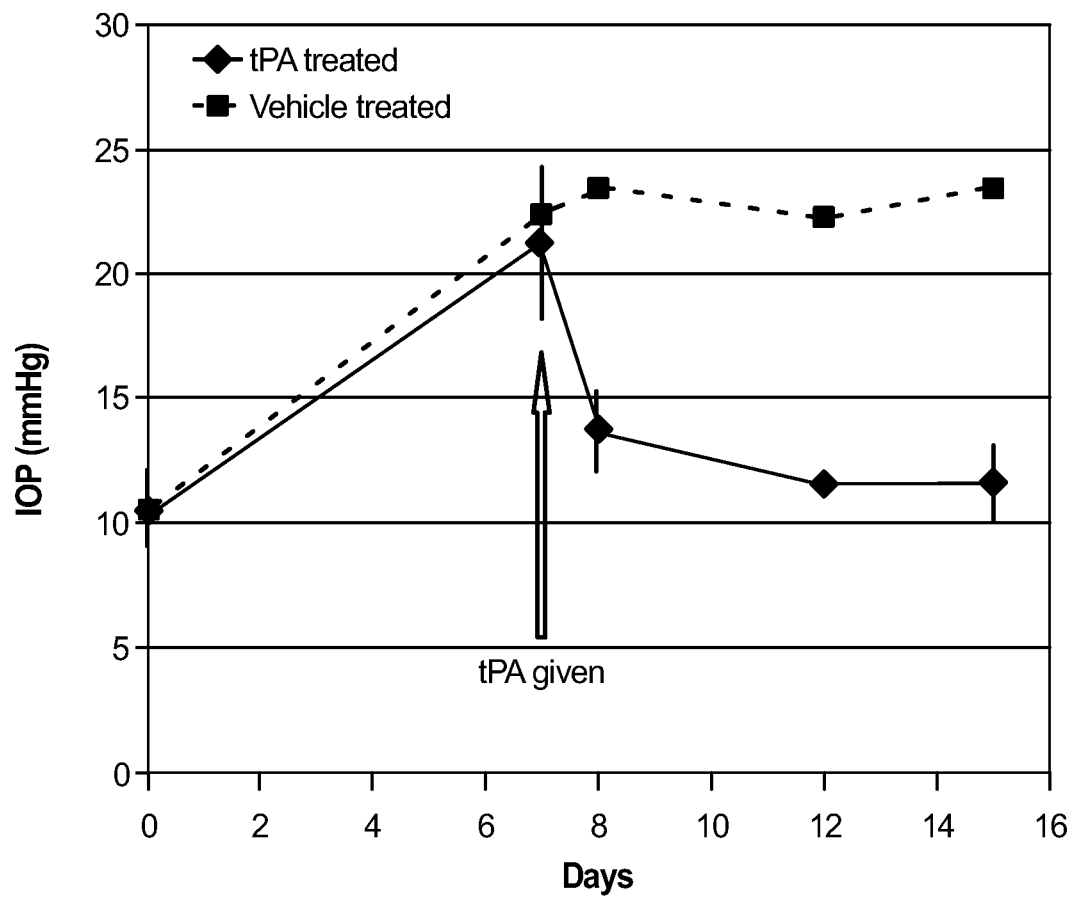
Figure 4C:
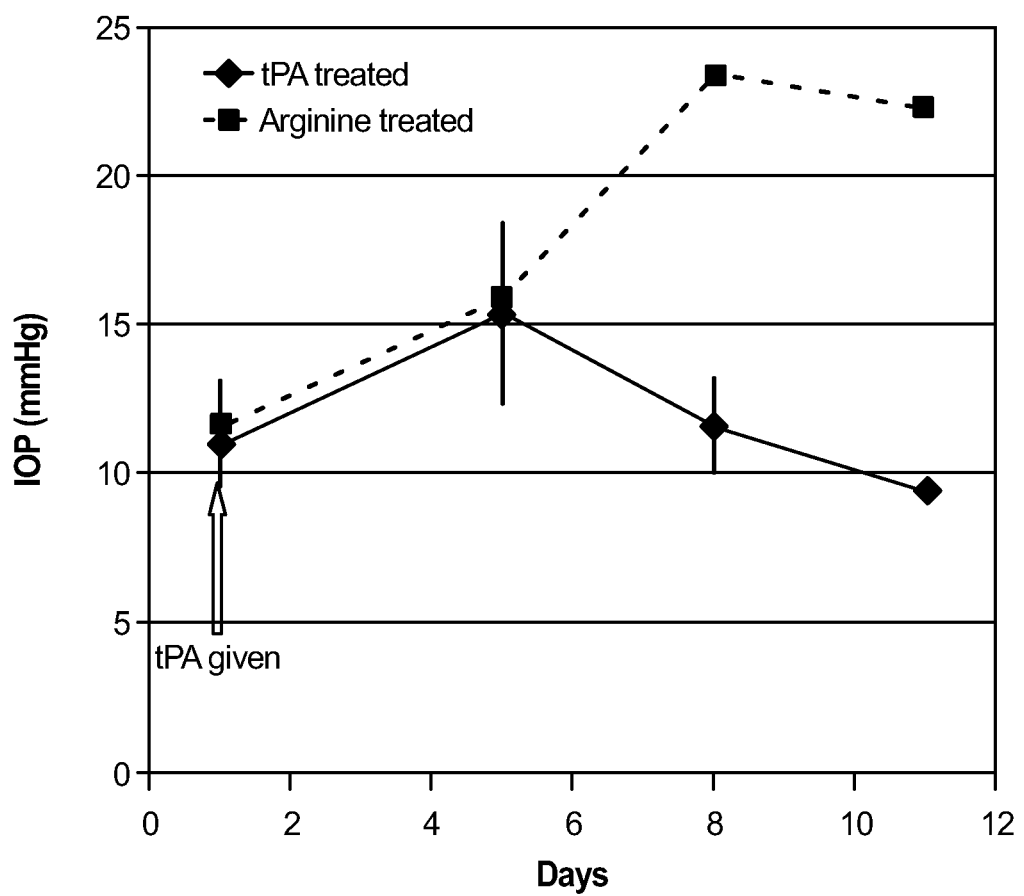

FIGS. 4A-4C. (A), Recombinant human tPA given as intravitreal injection can reverse IOP increase in sheep caused by steroid exposure. Steroids were administered to both eyes starting on Day 0 and tPA treatment commenced on Day 7. IOP (OD), IOP in control (left) eye treated with prednisolone only. IOP (OS), IOP in eye treated with prednisolone plus intravitreal tPA (right eye). Values are means+/−SEMs from 8 sheep. (B), The effect is not caused by the arginine present in the commercial tPA prep, as arginine administration alone does not alter steroid-increased IOP. (C), Administration of tPA prior to onset prevents IOP elevation. Representative experiment with 0.1 mg tPA injected into right eye (OD) and 4.23 mg arginine injected into left eye (OS) on Day 1; bilateral prednisolone instillations were also initiated on Day 1 and maintained through the end of protocol. tPA administration concurrent with steroid instillation kept outflow facility at normal levels.

Figure 5:
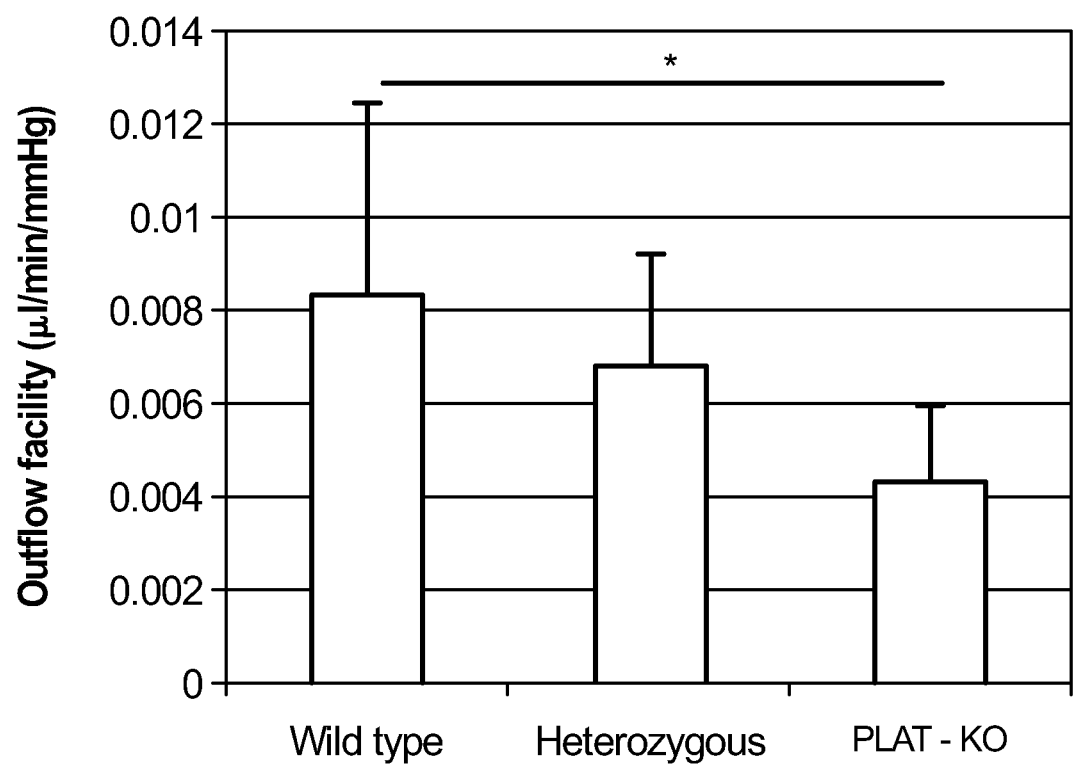
Figure 6A:
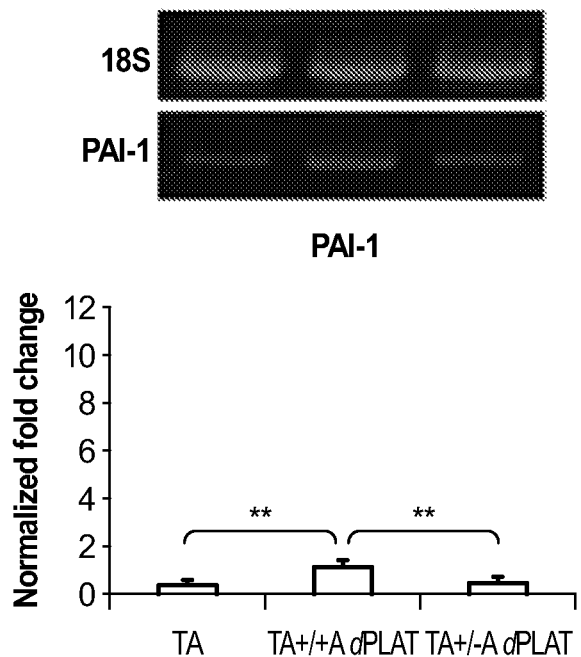
Figure 6B:
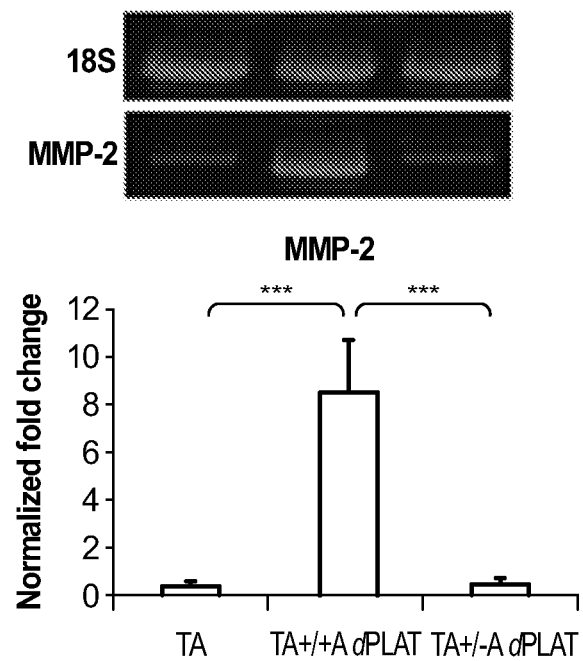
Figure 6C:
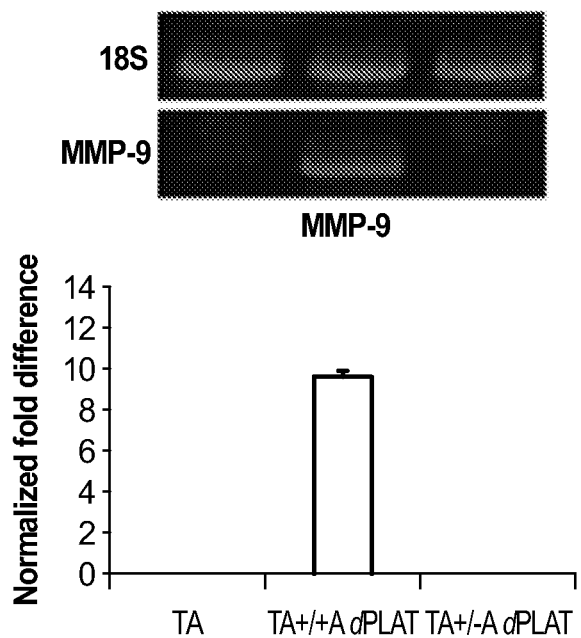
Figure 6D:
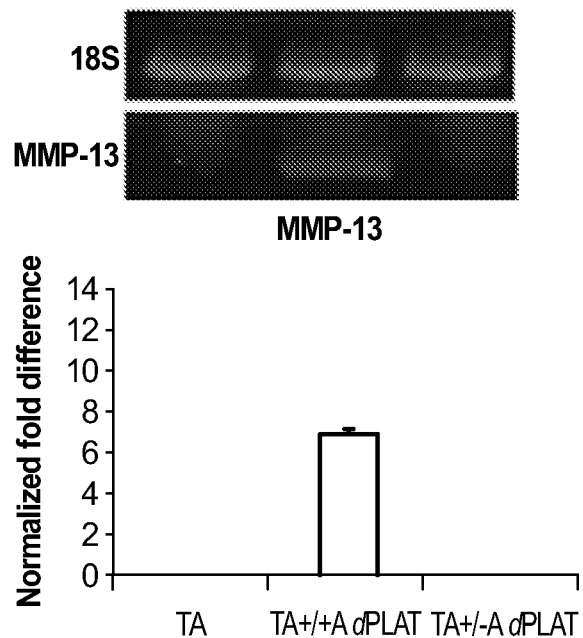

FIG. 5. Outflow facility in PLAT KO (N=10), heterozygote (N=4) and wild type mice (N=8). Difference between WT and KO animals is significant (ANOVA, p<0.05, Tukey post hoc analysis).

FIGS. 6A-6D. Normalized fold change (mean±SD) (panels A and B) and fold difference (panels C and D) in expression of PAI-1, MMP-2, MMP-9, MMP-13, in mouse angle rings receiving triamcinolone (TA) alone or TA with an adenovector carrying sheep PLAT. TA+/+AdPLAT: eyes with significant PLAT expression in the TM, TA+/−AdPLAT: eyes without significant PLAT expression in the TM Fold changes were compared to 1. Asterisks indicate statistically significant differences (p<0.01, *p<0.001, t-test).

Figure 7:
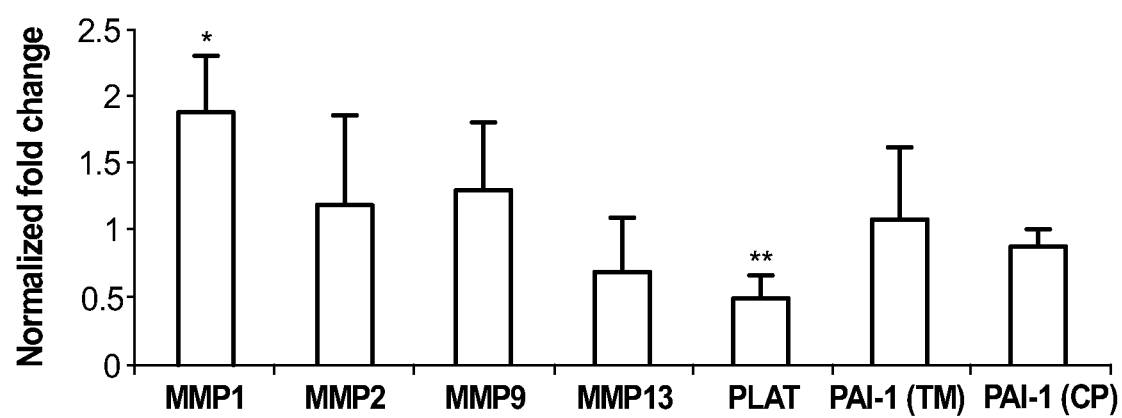

FIG. 7. Effect of tPA on gene expression in sheep. tPA acts through upregulation of specific MMPs.

Figure 8:
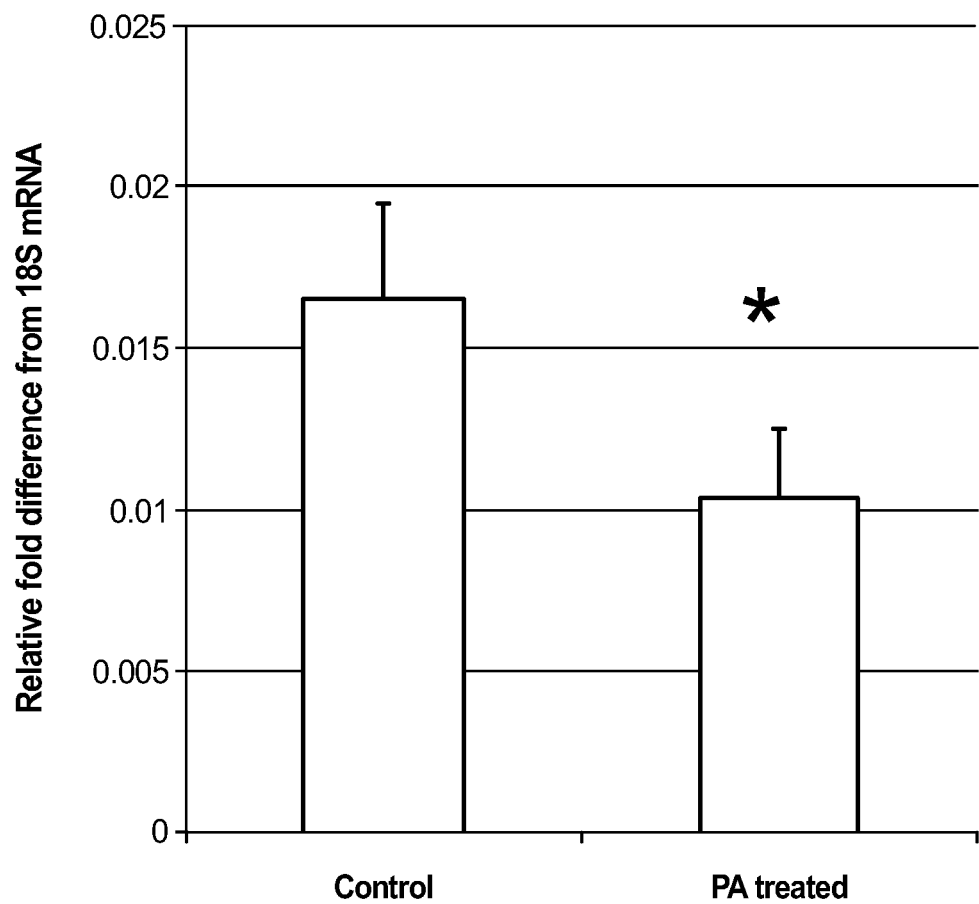

FIG. 8. Relative fold difference of PLAT mRNA from 18S mRNA amounts in HTM cells treated with prednisolone acetate (PA treated) or vehicle (Control) for 1 hour. Differences are statistically significant (p<0.05, t-test).

Figure 9:
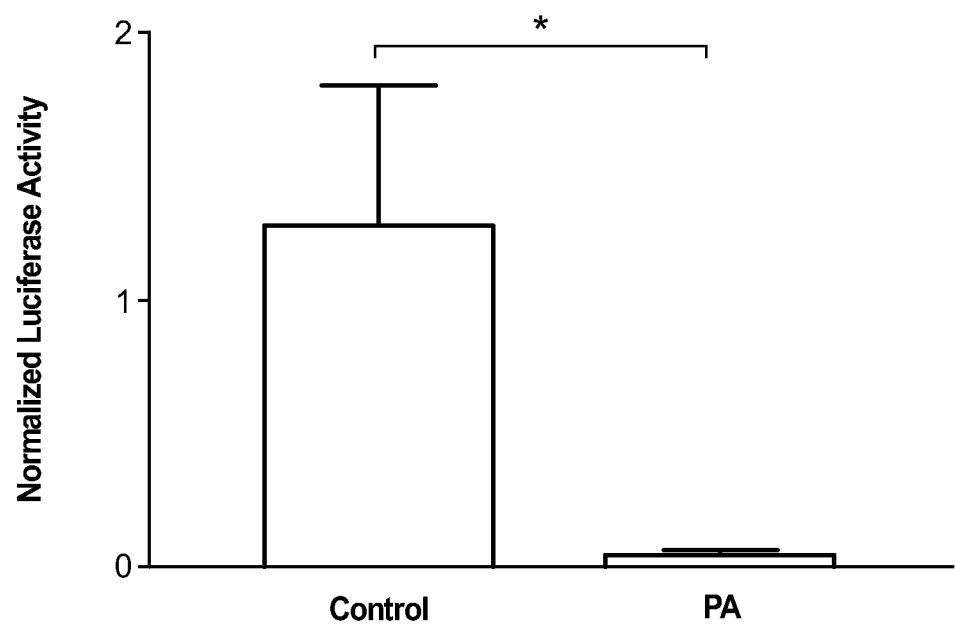

FIG. 9. Luciferase assay of PLAT promoter activity. A commercially available clone of the human PLAT promoter (Switchgear genomics) was used to transfect HTM cells using the nucleofector. Renila luciferase activity was measured 24 h after transfection in vehicle (Control) and prednisolone (PA) treated cells and normalized for cypridina activity in the medium.

DETAILED DESCRIPTION OF THE DISCLOSURE

The present disclosure presents direct administration, activation or upregulation of tissue plasminogen activator (tPA) as a useful method for the treatment of intraocular pressure (IOP)-associated conditions, such as glaucoma.

The inventors have discovered that tPA therapeutic agents can be used to lower IOP long-term even when there is no obvious fibrin accumulation. This is in contrast to short-term use of tPA as indicated for the purpose of reducing excess fibrin in acute settings, such as following glaucoma surgery. The inventors have determined that administration of tPA therapeutic agents over an extended period of time can lower IOP and treat glaucoma and other conditions associated with increased IOP.

Intraocular pressure (IOP), the fluid pressure within the eye, can be measured in units of millimeters of mercury (mmHg) or kilopascals (kPa). Normal intraocular pressure is typically considered to be between 10 mmHg and 20 mmHg. The average value of intraocular pressure is 15.5 mmHg with fluctuations of about 2.75-3.50 mmHg. Elevated intraocular pressure (above 21 mmHg or 2.8 kPa) is the most important and only modifiable risk factor for glaucoma.

As used herein, the term "IOP-associated conditions" refers to conditions of the eye that are associated with elevated intraocular pressure. Examples of IOP-associated conditions include, but are not limited to, ocular hypertension and glaucoma, including primary glaucomas such as closed angle glaucoma and open angle glaucoma. Other forms of glaucoma, such as the various forms of developmental glaucomas and secondary glaucomas such as steroid-induced glaucoma, pigmentary glaucoma and pseudoexfoliation glaucoma, are also IOP-associated conditions according to the invention. Chronic forms of IOP-associated conditions, such as chronic forms of glaucoma or chronic ocular hypertension, in which the condition and/or the elevated IOP persist for extended periods of time (i.e., a persistent IOP-associated condition or elevated IOP lasting at least 1 day to 4 weeks, 1 to 12 months, or a year or more), can be effectively managed by the disclosed invention. In a preferred embodiment, the IOP-associated condition is glaucoma, particularly steroid-induced glaucoma and/or open angle glaucoma.

The "tPA therapeutic agent" or a "composition of the invention" can include one or more of: tPA; tPA functional derivates or homologs; tPA variants, such as recombinant tPA, particularly recombinant human tPA; small molecule tPA agonists; RNA and other molecules that cause tPA up-regulation; and gene therapy vectors.

tPA. tPA is an enzyme involved in the breakdown of blood clots. tPA catalyzes the conversion of plasminogen to plasmin, the major enzyme responsible for clot breakdown. There are at least three splice variants of tPA. As an example, the sequence for a specific human tPA variant, isoform 1, is set forth in GenBank Accession No. NM_000930.3. In a second example, the sequence for another specific human tPA variants, isoform 3, is set forth in GenBank Accession No. NM_033011. Transcript variant 3 is 46 amino acids shorter than variant 1 as it lacks exon 4 as present in transcript variant 1. The absence of these amino acids in transcript 3 makes it unlikely this isoform can form a two chain disulfide linked protein, like isoform 1. tPA polypeptide variants can be naturally-occurring, recombinant, modified, or synthetic and can include derivatives, analogs, and fragments of the tPA variant amino acid sequence. In addition, tPA genetic variants include naturally-occurring, recombinant, modified, or synthetic nucleic acids encoding tPA polypeptide variants and include derivatives, analogs, and fragments of a tPA gene variant or isoform.

tPA functional derivatives. Functional derivatives and homologs of tPA are contemplated for use in the disclosed methods. As used herein, a "functional derivative" is a molecule which possesses the capacity to perform the biological function of tPA, i.e, a molecule that is able to functionally substitute for tPA, e.g., in the ability to catalyze the conversion of plasminogen to plasmin, improve outflow facility, and/or reduce elevated IOP. Functional derivatives include fragments, parts, portions, equivalents, analogs, mutants, mimetics from natural, synthetic or recombinant sources including fusion proteins. Derivatives may be derived from insertion, deletion or substitution of amino acids. Amino acid insertional derivatives include amino and/or carboxylic terminal fusions as well as intrasequence insertions of single or multiple amino acids. Insertional amino acid sequence variants are those in which one or more amino acid residues are introduced into a predetermined site in the polypeptide although random insertion is also possible with suitable screening of the resulting product. Deletional variants are characterized by the removal of one or more amino acids from the sequence. Substitutional amino acid variants are those in which at least one residue in the sequence has been removed and a different residue inserted in its place. Additions to amino acid sequences include fusions with other peptides, polypeptides or proteins.

A "homolog" is a protein related to a second protein by descent from a common ancestral DNA sequence. A member of the same protein family (for example, the tPA family) can be a homolog. A "functional homolog" is a related protein or fragment thereof that is capable of performing the biological activity of the desired gene, i.e, is able to functionally substitute for tPA. Homologs and functional homologs contemplated herein include, but are not limited to, polypeptides derived from different species.

A functional derivative or homolog can have 75%, 80%, 85%, 90%, 95% or greater amino acid sequence identity to a known tPA amino acid sequence, or 75%, 80%, 85%, 90%, 95% or greater amino acid sequence identity to a tPA variant thereof.

tPA variants and homologs. A "variant" refers to a molecule substantially similar in structure and function to either the entire molecule, or to a fragment thereof. Thus, as the term variant is used herein, two molecules are variants of one another if they possess a similar activity even if the structure of one of the molecules is not found in the other, or if the sequence of amino acid residues is not identical. The term variant includes, for example, splice variants or isoforms of a gene. Equivalents should be understood to include reference to molecules which can act as a functional analog or agonist. Equivalents may not necessarily be derived from the subject molecule but may share certain conformational similarities. Equivalents also include peptide mimics.

tPA variants include recombinant tissue plasminogen activators (r-tPAs) such as alteplase, reteplase, tenecteplase, and desmoteplase. Reteplase is a recombinant non-glycosylated form of htPA modified to contain 357 of the 527 aminoacids. Tenecteplase is a recombinant fibrin-specific plasminogen activator derived from native t-PA by modifications at three sites of the protein structure. Both reteplase and tenecteplase are FDA approved. Other investigational molecules exist with similar activity, some of them modified ($2^{nd}$ and $3^{rd}$ generation) rtPAs, some are molecules that share similarities with tPA but come from other organisms, for example, anistreplase, duteplase, monteplase, lanoteplase, pamiteplase, amediplase, desmoteplase, staphylokinase, snake venom plasminogen activators such as TSV-PA (*Trimeresurus stejnegeri* venom plasminogen activator), Haly-PA (*Agkistrodon halys* venom plasminogen activator), LV-PA (*Lachesis muta muta* venom plasminogen activator), and recombinant chimeric tPAs such as GHRP-SYQ-K2S (which includes the tPA kringle 2 domain, K2S, and the tPA serine protease domain, glycyl-histidyl-arginyl-prolyl) and GHRP-scu-PA-32K (glycyl-histidyl-arginyl-prolyl-single-chain urokinase-type plasminogen activator). For review see Flemmig and Melzig (Flemmig, M., et al., J Pharm Pharmacol 64(8):1025-1039 (2012)), the contents of which are incorporated by reference herein.

A "tPA agonist" is a molecule that increases the expression, activity or function of tPA. For example, a compound can act as a tPA activator by increasing or enhancing tPA expression or activity, or increasing or enhancing the tPA-mediated catalysis of plasminogen to plasmin. Examples of tPA agonists include peptides, polypeptides, proteins, antibodies, small molecules, chemotherapeutic agents, and fragments, derivatives and analogs thereof, that increase or enhance the expression, activity or function of tPA.

Small molecule tPA agonists. A number of small molecules are known to be tPA agonists, including, but not limited to:

a. 20-S-Hydroxycholesterol and other oxysterols (Sonic-Hedghog activators) (Xin, H., et al., *J Cereb Blood Flow Metab* 31(11):2181-2188 (2011)), (Dwyer, J. R., et al., *J Biol Chem* 282(12):8959-8968 (2007))
b. N-acetyl-cysteine (Chu, D. I. et al., *Surgery* 149(6):801-812 (2011))
c. Neovastat (CAS Registry No. 305838-77-1) (Gingras, D., et al., *Biochem Biophys Res Commun* 320(1):205-212 (2004))
d. Nicotine (Katono, T., et al., *Arch Oral Biol* 54(2):146-155 (2009))
e. Allopregnanolone (3α,5α-tetrahydroprogesterone) (VanLandingham, J. W., et al., *J Cereb Blood Flow Metab* 28(11):1786-1794 (2008))
f. Testosterone (Guo, J., et al., *Endocrine* 32(1):83-89 (2007))
g. Forskolin (Guo, J., et al., *Endocrine* 32(1):83-89 (2007))
h. L-threo-DOPS (L-threo-dihydroxyphenylserine) (Mataga, N., et al., *Neurosci Lett* 218(3):149-152(1996))
i. Pituitary adenylate cyclase-activating polypeptide (PACAP) (Raoult, E., et al., *J Neurochem* 119(5):920-931 (2011))
j. PDE4 activators (e.g., Iloprost, CAS Registry No. 73873-87-7) (Yang, F., et al., *Thromb Res* 129(6):750-753 (2012))
k. 5-azacytidine (Griffiths, J. B., et al., *Dev Biol Stand* 66:417-422 (1987))
l. CPT-cAMP (CAS Number 129735-01-9) (Heaton, J. H., et al., *Mol Endocrinol* 3(1):185-192 (1989))
m. Retinoic acid (Benjamin, L. A., et al., *Cancer Chemother Pharmacol* 25(1):25-31 (1989))
n. Phorbol esters (Grulich-Henn, J., et al., *Blut* 61(1):38-44 (1990))
o. 8-bromo-cAMP (Heaton, J. H., et al., *Mol Endocrinol* 4(1):171-178 (1990))
p. 2-diocynoyl-sn-glycerol (diC8) (Grulich-Henn, J., et al., *Blut* 61(1):38-44 (1990))
q. Phorbol 12 myristate 13 acetate (PMA) (Grulich-Henn, J., et al., *Blut* 61(1):38-44 (1990))

r. Interleukin 1 antagonists (e.g., AF12198, CAS Registry No. 185413-30-3) (Bevilacqua, M. P., et al., *J Clin Invest* 78(2): 587-591 (1986))
s. Epac1 inhibitors (e.g., the tetrahydroquinoline analog CE3F4) (Courilleau, D., et al., *J Biol Chem* 287(53): 44192-44202 (2012))
t. Prostaglandin E2 (PGE2) (Markosyan, N., et al., *Endocrinology* 150(1):435-444 (2009))
u. Butyrate (Reinders, J. H., et al., *Ann N Y Acad Sci* 667:194-198 (1992))
v. 1,25-dihydroxyvitamin D-3 (Fukumoto, S., et al., *Biochim Biophys Acta* 1201(2):223-228 (1994))
w. Estradiol and estrogen analogues (Davis, M. D., et al., *J Steroid Biochem Mol Biol* 52(5):421-430 (1995))
x. Laminin (Sonohara, S., et al., *Int J Cancer* 76(1):77-85 (1998))
y. Interleucin-6 (IL-6) (Hosoya, S., et al., *J Endod* 24(5): 331-334 (1998))
z. Ascorbic acid (Yoshino, A., et al., *Life Sci* 70(12):1461-1470 (2002))
aa. Sesamol (Chen, P. R., et al., *J Nutr Biochem* 16(1):59-64 (2005))
bb. Lysophosphatidylcholine (Sheikh, A. M., et al., *Biochem Biophys Res Commun* 329(1):71-77 (2005))

Many of these molecules have been shown to increase tPA in various cells in culture or in vivo.

It is a subject of this invention that tPA therapeutic agents of the invention preferably upregulate tPA expression, function, or activity in the trabecular meshwork (TM), an important area of the eye for regulating IOP. tPA activity in the TM would be particularly effective to reduce IOP.

RNA molecules that cause tPA up-regulation. In addition, a tPA therapeutic agent can be an RNA molecule that up-regulates tPA expression. Such molecules include antisense oligonuleotides, ribozymes, and/or short interfering RNA (siRNA) directed against genes that negatively regulate tPA, such that reduced expression of these negative regulators causes increased expression or activity of tPA. Negative regulators of tPA include the genes encoding for Tenascin C, Hypoxia Inducible Factor 1 (HIF1), Exchange Protein directly Activated by cAMP (EPAC1), interleukin 1 and Patched 1.

Gene therapy. Gene therapy vectors can be any vector that can effectively increase tPA expression in the eye. Many vectors useful for transferring exogenous genes into target mammalian cells are available. The vectors may be episomal, e.g. plasmids or virus derived vectors such cytomegalovirus vector, adenoviral vector, adeno-associated viral (AAV) vector, etc., or the vectors may be integrative, e.g., integrating the reprogramming gene into the target cell genome, through homologous recombination or random integration, e.g. retrovirus derived vectors such MMLV (Moloney Murine Leukemia Virus), HIV-1, ALV (Avian leukosis virus), or lentiviral vectors.

In one embodiment, a vector for expressing a tPA therapeutic gene comprises a promoter operably linked to the tPA therapeutic gene. The phrase "operably linked" or "under transcriptional control" as used herein means that the promoter is in the correct location and orientation in relation to a polynucleotide to control the initiation of transcription by RNA polymerase and expression of the polynucleotide. Several promoters are suitable for use in the vectors for expressing the reprogramming factor, including, but not limited to, RNA pol I promoter, RNA pol II promoter, RNA pol III promoter, and cytomegalovirus (CMV) promoter. Other useful promoters are discernible to one of ordinary skill in the art. In some embodiments, the promoter is an inducible promoter that allows one to control when the tPA therapeutic gene is expressed. Suitable examples of inducible promoters include tetracycline-regulated promoters (tet on or tet off) and steroid-regulated promoters derived from glucocorticoid or estrogen receptors. Constitutive expression of a tPA therapeutic gene can be achieved using, for example, expression vectors with a CMV, CAG (chicken beta-actin promoter with CMV enhancer), or PGK (phosphoglycerate kinase 1) promoter. Inducible expression of a tPA therapeutic gene can be achieved using, for example, a tetracycline responsive promoter, such as the TRE3GV (Tet-response element 3rd generation) inducible promoter (Clontech Laboratories, Mountain View, Calif.). Alternatively, the promoter operably linked to the tPA therapeutic gene may be a promoter that is activated in specific cell types and/or at particular points in development.

Depending on the promoter used, expression of a tPA therapeutic gene can be constitutive (continuous expression of the factor) or inducible (capable of being turned on and off). Expression can also be transient, that is, temporary expression of the tPA therapeutic gene over a limited time span. Transient expression may be achieved by use of a non-integrative vector, where the vector is lost from the cell or cell population over time, or by use of an inducible promoter in an integrative or non-integrative vector that can be manipulated to cease expression of the reprogramming gene after a period of time. In a specific embodiment, expression of a tPA therapeutic gene is inducible.

Suitable vectors can contain markers to identify and/or select transformed cells. Examples of selectable markers include visual markers such as green fluorescent protein (GFP), red fluorescent protein (RFP), or fluorescein; epitope markers such as His, c-myc, GST, Flag, or HA tags; enzymatic/nutritional markers such as DHFR (dihydrofolate reductase); or antibiotic resistance markers such as neomycin, puromycin, blasticidin, or hygromycin.

Preferred gene therapy vectors include AAV2 vectors, preferably self-complimentary AAV2 (scAAV2) vectors, and lentivirus vectors, encoding the tPA gene. AAV2 and lentivirus vectors can provide long term expression of proteins in the TM. The inventors have used lentiviral vectors to express proteins in the TM in animals. Expression can be maintained for at least a period of months and can last for years. ScAAV2 vectors have also been used for the long-term transfection of animals (up to 2 years) without adverse effects. Because of the size of the gene encoding the tPA native protein, scAAV vectors may not be able to accommodate the whole insert, requiring alternative strategies for delivery of the transgene. However, the message for modified tPA proteins that are smaller in size can be packaged in scAAV2. For gene therapy experiments it is important to incorporate controls that will allow the cessation of expression if needed (and potentially to also allow exogenous induction of expression). These controls can be encoded in the genetic material and can, for example, include Tetracycline- or tamoxifen-inducible repression systems.

Gene therapy encompasses expression of any tPA or tPA variant or derivative, as well as expression of a gene encoding a positive regulator of tPA, or encoding a naturally-occurring, recombinant, modified, or synthetic protein, variant or derivative or other molecule that up-regulates tPA, or encoding a negative regulator of a gene that negatively regulates tPA. Positive regulators of tPA include Sonic Hedgehog (Shh), protein kinase A, laminin and interleukin 6.

Genes for molecules that downregulate expression of tPA ("tPA inhibitors") can be perturbed by antisense oligonucleotides, siRNA or ribozymes. Thus, antisense oligonucleotides, siRNA or ribozymes that reduce or prevent expression of inhibitors that downregulate tPA are also contemplated as tPA therapeutic agents. Genes that downregulate tPA include, but are not limited to:
a) Tenascin C (Brellier, F., et al., *FEBS Lett* 585(6):913-920 (2011)).
b) HIF1 (Zhu, G., et al., *Osteoarthritis Cartilage* 17(11): 1494-1502 (2009)).
c) Epacl (Yang, F., et al., *Thromb Res* 129(6):750-753 (2012)).
d) Interleukin 1 (Bevilacqua, M. P., et al., *J Clin Invest* 78(2): 587-591 (1986)).
e) Patched 1. Patched 1 is inhibited by sonic hedgehog (SHH); SHH upregulates tPA by inhibiting Patched 1 (Xin, H., et al, *J Cereb Blood Flow Metab* 31(11): 2181-2188 (2011)).

Methods of treatment. This disclosure presents methods for the treatment of IOP-associated conditions, by administering an effective amount of a tPA therapeutic agent to a subject in need thereof. The tPA therapeutic agent can be administered to the subject for as long as the condition and/or elevated IOP persists, in any manner that provides extended administration of the tPA therapeutic agent and/or long-term reduction of IOP. A "reduction" or "lowering" of IOP encompasses reduction of IOP to within normal levels of 10-20 mmHg, or any lowering of IOP, such as by 3, 5, 8, or 10 mmHg or more in a subject, relative to before treatment of said subject was commenced. "Long-term reduction" in IOP can be a reduction in IOP lasting 1 day to 4 weeks, 1 to 12 months, or a year or more. Extended administration includes, but is not limited to, less frequent administration of a composition that provides extended release or extended expression of a tPA therapeutic agent, or more frequent administration of a composition that provides shorter acting release or expression of a tPA therapeutic agent.

In the methods contemplated herein, the tPA therapeutic agents can be administered for at least 1, 2, 3, 4, 5, 6, 7, or 8 weeks, or for at least 1, 2, 3, 4, 5, 6, 7, 8, 9, 10, 11, or 12 months, or at least 1, 2, 3, 4, or 5 years. As part of the extended administration, the tPA therapeutic agent can be administered on a recurrent or repeated basis, such as on a daily, weekly, bi-weekly, monthly, bi-monthly, or on an annual basis, to provide a reduction in IOP over periods of time such as 1 day to 4 weeks, 1 to 12 months, or a year or more. This recurrent basis differs from prior art suggestion to administer tPA to treat acute fibrin build-up, such as administration of a single or limited number of intraocular tPA injections, in the immediate post-operative period following ocular surgery, to reverse fibrin accumulation. Prior to the instant invention, tPA administration in the absence of fibrin accumulation, or extended tPA treatment as a long-term solution to the problem of chronic elevated IOP, had not been suggested in the art. However, the disclosure herein encompasses both tPA administration even where excess fibrin accumulation is not apparent, and extended tPA treatment as a long-term solution to the problem of chronic elevated IOP.

Alternatives to arginine formulations: Although unmodified recombinant tPA is formulated with L-Arginine, other modified tPAs, such as reteplase, tenecteplase, and other tPA functional derivatives, as discussed above, do not use Arginine. Formulas encompassing tPA therapeutic agents, including tPA, tPA functional derivatives and variants, and small molecule tPA therapeutic agents, in a formulation with low or no Arginine, are preferred in the methods of the invention.

As used herein, the terms "subject" and "patient" are used interchangeably and refer to an animal, preferably a mammal such as a non-primate (e.g., cows, pigs, horses, cats, dogs, rats etc.) and a primate (e.g., monkey and human), and most preferably a human.

As used herein, "treatment" refers to clinical intervention in an attempt to alter the disease course of the individual or cell being treated. Therapeutic effects of treatment include without limitation, preventing recurrence of disease, alleviation of symptoms, diminishment of any direct or indirect pathological consequences of the disease, decreasing the rate of disease progression, amelioration or palliation of the disease state, and remission or improved prognosis. For example, treatment of a glaucoma patient can include lowering IOP and/or preventing, reducing, or ameliorating eye pain, optic nerve damage, retinal cell damage, or retinal cell loss. Although lowering IOP is preferably lowering IOP to within normal levels of 10-20 mmHg, any lowering of IOP, such as by 1-10 mmHg, 10-20 mmHg, or 20 mmHg or more in a subject, relative to before treatment was commenced, is considered to be effective.

The inventors have determined that administration of a tPA therapeutic agent can improve aqueous humor outflow in the eye. Aqueous humor is the clear, watery fluid that fills the complex space in the front of the eye which is bounded at the front by the cornea and at the rear by the front surface or face of the vitreous humor. Production, circulation, and drainage of aqueous humor into and out of the anterior chamber of the eye maintains the IOP at a relatively constant level.

The trabecular meshwork is the sponge-like tissue located near the cornea and iris that functions to drain the aqueous humor from the eye. The trabecular meshwork offers a certain resistance to the outflow of aqueous humor that is needed to maintain a steady-state IOP. The inverse of this resistance is trabecular outflow facility, a measure of the compliance of the trabecular meshwork. In glaucomatous eyes the resistance to aqueous humor outflow is increased due to an increase in different forms of extracellular material deposited within the meshwork, which decreases outflow facility. The inventors have found that tPA therapeutic agents can increase the outflow facility of the trabecular meshwork, which improves IOP and reduces the risk of, or directly treats, IOP-related conditions.

As used herein, the terms "therapeutically effective amount" and "effective amount" are used interchangeably to refer to an amount of a composition of the invention that is sufficient to result in the prevention of the development, recurrence, or onset of an IOP-associated condition and one or more symptoms thereof; enhance or improve the prophylactic effect(s) of another therapy; reduce the severity and duration of an IOP-associated condition; ameliorate one or more symptoms of an IOP-associated condition, in particular to lower IOP and/or improve outflow facility; prevent the advancement of an IOP-associated condition; cause regression of an IOP-associated condition; and/or enhance or improve the therapeutic effect(s) of additional treatment(s) administered to ameliorate an IOP-associated condition.

A therapeutically effective amount can be administered to a patient in one or more doses sufficient to palliate, ameliorate, stabilize, reverse or slow the progression of the IOP-associated condition, or otherwise reduce the pathological consequences of the condition, or reduce the symptoms of the condition. The amelioration or reduction need not be permanent, but may be for a period of time ranging from at least one hour, at least one day, or at least one week or more. The effective amount is generally determined by the physician on a case-by-case basis and is within the skill of one in the art. Several factors are typically taken into account when determining an appropriate dosage to achieve an effective amount. These factors include age, sex and weight of the patient, the condition being treated, the severity of the condition, as well as the route of administration, dosage form and regimen and the desired result.

Administration to a subject in need of treatment. The tPA therapeutic agent or composition of the invention can be administered to an eye of a patient as solutions, suspensions, or emulsions (dispersions). For example, the composition can be delivered topically to the eye in the form of drops, sprays, or gels. It can also be absorbed into contact lens or other non-biodegradable or biodegradable material that is placed on the cornea or conjunctiva. Alternatively, the composition can be administered by injection (e.g., intravitreal, intraorbital, subconjunctival, and/or sub-tenon injection). The composition can also be administered by means of an implantable device, which can be attached, for example, to a subconjunctival, anterior chamber or vitreous region of the eye. For administration to a patient, the agent or composition is prepared with pharmaceutically acceptable opthalmologic carriers, excipients, or diluents.

Other ingredients which may be desirable to use in the ophthalmic preparations of the present invention include preservatives, co-solvents, buffers, viscosity building agents and penetration enhancers. Viscosity building agents, such as hydroxymethyl cellulose, hydroxyethyl cellulose, methylcellulose, polyvinylpyrrolidine, a polymer matrix such as CAPA4101 or the like, may be added to the compositions of the present invention to improve the retention of the compound in the conjunctival sac or surrounding area. In order to prepare sterile ophthalmic ointment formulations, the tPA therapeutic agent may be combined with a preservative in an appropriate vehicle, such as white petroleum, mineral oil or liquid lanolin. Sterile ophthalmic gel formulations may be prepared by suspending the tPA therapeutic agent in a hydrophilic base prepared from the combination of, for example, carbopol-940, or the like, according to the methods known in the art for other ophthalmic formulations.

Protein molecules like tPA or modified tPA functional derivatives are preferably administered intraocularly, as their penetration of the ocular wall is limited. Intracameral injections (injections into the anterior chamber) are easier to perform, but proteins injected there are cleared fairly rapidly. Proteins injected intravitreally are eliminated in large part (~70%) through the anterior chamber. Because diffusion in the vitreous is delayed, proteins injected there have a longer duration of action. For this reason, intravitreal injection of tPA agents is preferred for intraocular injection. Formulations of tPA and tPA analogues and functional derivatives, for injection and administration by other routes, are known in the art.

The inventors have determined that, in a sheep model of elevated IOP, the effect of a single tPA injection on IOP lasted for approximately 18 days. Administration in subjects such as humans are expected to show a similar time frame for effect on IOP (i.e., two to three weeks). Recurrent (for example, monthly) intravitreal injections are widely accepted for therapy of other ocular conditions (like macular degeneration), but are more involved and carry a higher risk for infection. Therefore, although recurrent injections of a tPA therapeutic agent are encompassed by the invention, the skilled artisan or doctor must weigh the benefit of such repeat injections with the potential negative effects.

Other sites and modes of administration include topical administration, administration via iontophoresis; implantation of cells that are genetically engineered to constantly produce a tPA therapeutic agent; implantation of slow release device; and subconjunctival administration. A review of methods for administration of ophthalmic drugs is found in Kompella, et al., *Ther Deliv* 1:435-456 (2010), the contents of which are incorporated by reference.

Topical administration: Although tPA has been shown to penetrate the cornea, administration via this mode has the disadvantage of limited penetration. In addition a significant amount of the tPA therapeutic agent may be released in the tears, potentially causing side effects in the nasal cavity and upper respiratory system.

Administration via iontophoresis: a tPA therapeutic agent can be administered iontophoretically. Iontophoresis utilizes low currents to enhance the penetration of charged molecules across tissue barriers. The drug is applied using an electrode carrying the same charge as the drug. An electrode with the opposite charge placed elsewhere in the body completes the circuit. The ionized drug molecule penetrates the tissue by electric repulsion. Additionally, neutral molecules can potentially be delivered using iontophoresis on the basis of electro-osmosis or solute-associated fluid transport. Commerically available iontophoresis devices include OCUPHOR (Iomed Inc., USA) and VISULEX (Aciont Inc., USA). Such delivery method will avoid some of the problems of topical administration while minimizing effects on the posterior segment of the eye.

Implantation of cells that are genetically engineered to constantly produce a tPA therapeutic agent: cells that are genetically engineered to produce a tPA therapeutic agent can be implanted within the eye. Such engineered cells may, for example, reside within a permeable device that allows diffusion of their protein products in the eye (such as Encapsulated Cell Technology, available from Neurotech Pharmaceuticals). Such a device or cells can be implanted surgically in the posterior or anterior segment of the eye and provide for extended administration of specific doses of tPA.

Implantation of slow release devices: a tPA therapeutic agent formulated in a slowly biodegradable substrate, for example, poly(lactic-co-glycolic) acid PLGA) or polylactic acid (PLA), can be implanted in the anterior (or posterior) segments surgically and allowed to release tPA therapeutic agent over long periods of time (up to, or even more than, 2 years). The device can also reside outside the eye (in the subconjunctival space) and connect with the anterior chamber (AC) via a small tube. In such case discharge of the medication can be controlled externally, and the device can be refillable.

Subconjunctival administration (injection through the conjunctiva) is also contemplated herein.

Small molecules that stimulate increased expression of tPA can be delivered by all of the above methods as well as orally. In one embodiment, small molecules are delivered topically.

Dosage of tPA therapeutic agents. tPA has been used in acute situations by intracameral injection usually at a dosages of 10-25 µs (Kim, M. H., et al., *Ophthalmic Surg Lasers* 29(9):762-766 (1998), Wu, T. T., et al., *Eye* (Lond) 23(1): 101-107 (2009)). For intravitreal use it has been used to dissolve sub-macular hemorrhages at a dosage of 30-100 µs (Chen, C. Y., et al., *Retina* 27(3):321-328 (2007)). Retinal toxicity has been reported with doses above 50-100 µs, but toxicity was attributed to the presence of arginine in the commercial preparations (Chen, S. N., et al., *Ophthalmology* 110(4):704-708 (2003), Oh, H. S., et al., *Curr Eye Res* 30(4):291-297 (2005)). For extended administration of tPA, and tPA variants and functional derivates such as reteplase, tenecteplase, and other modified tPAs, injections of 10-120 μg per treatment, preferably 30-100 μg per treatment, even more preferably 25-50 μg, can be administered to a subject in need of treatment. In some embodiments, tPA therapeutic agents as disclosed herein are administered at dosages of 10, 20, 25, 30, 35, 40, 45, 50, 55, 60, 65, 70, 75, 80, 85, 90, 95, 100, 110, or 120 μs per dose. The doctor or skilled artisan can modify these dosages appropriately.

This disclosure also encompasses very low dose administration in a slow-release formulation or device. The inventors have achieved a reduction in IOP with a single dose of 1 ng of tPA injected intracamerally. Turnover of aqueous is approximately 120 minutes, so the injected agent is completely gone by 120 minutes. Assuming a linear model of elimination, in 30 minutes there would be 75% (of 1 ng) present. Thus the low dosage formulations and devices disclosed herein would release approximately 1 ng or more every 30 minutes. Accordingly, the slow release device disclosed herein provides continuous release of 0.1-5 ng, preferably 1 ng, of tPA therapeutic agent every 30 minutes. That means release rate should be about 20-100 ng/day, preferably 40-80 ng/day, most preferably about 48-50 ng/day.

Throughout this application, the terms "about" and "approximately" indicate that a value includes the inherent variation of error for the device, the method being employed to determine the value, or the variation that exists among the study subjects. In one non-limiting embodiment the terms are defined to be within 10%, preferably within 5%, more preferably within 1%, and most preferably within 0.5%.

For example, based on continuous administration of 48-50 ng/day, a 6 month continuous delivery of tPA therapeutic agent would contain approximately 9000 ng (9 μg) of tPA therapeutic agent. Accordingly, a concentration of 9 μg tPA per 2 μl formulation, or about 5 μg/μl, or 5 about mg/ml, is placed, for example, inside a 1×1×2 mm device. Currently tPA therapeutic agents are administered as solution, but solid forms are contemplated for administration in a slow release device.

The present disclosure encompasses treating IOP-associated conditions, such as glaucoma, by upregulating tPA but also by downregulating plasminogen activator inhibitors 1 (PAI1) and 2 (PAI2). Thrombin is a known upregulator of tPA while metformin, and PPAR agonists (like troglitazone and rosiglitazone) are known antagonists of the PAIS. In addition statins are known to downregulate PAIS systemically and can be used either systemically or topically to modulate this system. Other activators of tPA have also been described, as well as other small molecules that inhibit PAIS and can be used for the same purposes. Statins also have direct effects on tPA activation (Essig, M., et al., *Circ Res* 83(7):683-90 (1998a), Essig, M., et al., *J Am Soc Nephrol* 9(8):1377-88 (1998b), Asahi, M., et al., *J Cereb Blood Flow Metab* 25(6): 722-9 (2005), Aarons, C. B., et al. *Ann Surg* 245(2):176-84 (2007)), in some instances without affecting PAIS.

The present disclosure is further illustrated by the following non-limiting examples.

EXAMPLES

Example 1

Treatment of Mice with Gene Therapy

Methods: Adenoviral vectors carrying cDNA of the sheep PLAT gene and a fluorescent reporter gene (mCherry) (AdPLAT) or with no transgene (AdNull) were created. Transgene expression was driven by the CMV promoter. 3 groups of C57/B6 mice received either: (1) 20 μl of triamcinolone acetonide (TA) suspension (40 mg/ml) subconjunctivally bilaterally followed immediately by unilateral intracameral injection with 2 μl AdPLAT (3-4×10$^{12}$ VG/ml); (2) 20 μl TA subconjunctivally bilaterally followed one week later by unilateral intracameral injection with 2 μl AdPLAT; or (3) 20 μl TA subconjunctivally bilaterally followed immediately by bilateral injection with 2 μl adenovirus AdNull. IOP was measured preterminally. Outflow facility was determined using simultaneous pressure and flow measurements (see FIGS. 2A-2C). After outflow facility measurement, all AdPLAT injected eyes were dissected and viewed under a fluorescent microscope to inspect for mCherry expression in the trabecular meshwork (TM). Eyes that showed mCherry expression were analyzed as a separate group from eyes that showed minimal mCherry expression.

Results. IOP was not significantly different between all eye groups (p>0.05) after either one or two weeks of treatment with TA steroid. Eyes subjected to one week of TA treatment that showed mCherry/PLAT expression (TA+AdPLAT) had 63%, 54%, and 31% higher outflow facility than AdPLAT treated eyes with minimal mCherry/PLAT expression (TA+/−AdPLAT), contralateral control eyes, and AdNull treated eyes, respectively. In animals injected with AdPLAT concurrently with TA, the mean±standard deviation (SD) outflow facility in AdPLAT injected eyes showing robust mCherry expression (TA+/+AdPLAT) (n=12), AdPLAT injected eyes showing minimal or no mCherry expression (TA+/−AdPLAT) (n=8), and contralateral eyes injected with TA alone (TA) (n=22) was 0.0097±0.0033, 0.0062±0.0022, and 0.0060±0.0025, respectively, while eyes that received both TA and AdNull concurrently (TA+AdNull) (n=30) had outflow facility of 0.0071±0.0023 (ANOVA, p<0.05). See FIGS. 1A-1B.

Eyes subjected to two weeks of TA treatment that showed mCherry/PLAT expression had 86% and 58% higher outflow facility than AdPLAT treated eyes with minimal mCherry/PLAT expression and contralateral control eyes respectively. In animals receiving AdPLAT one week after TA injection, the mean±SD outflow facility in TA+/+AdPLAT (n=6), TA+/−AdPLAT (n=11) and TA (n=24) eyes was 0.0109±0.0026, 0.0062±0.0027, and 0.0067±0.0028, respectively (ANOVA, p<0.05). See FIGS. 1A-1B.

Figure 1A:
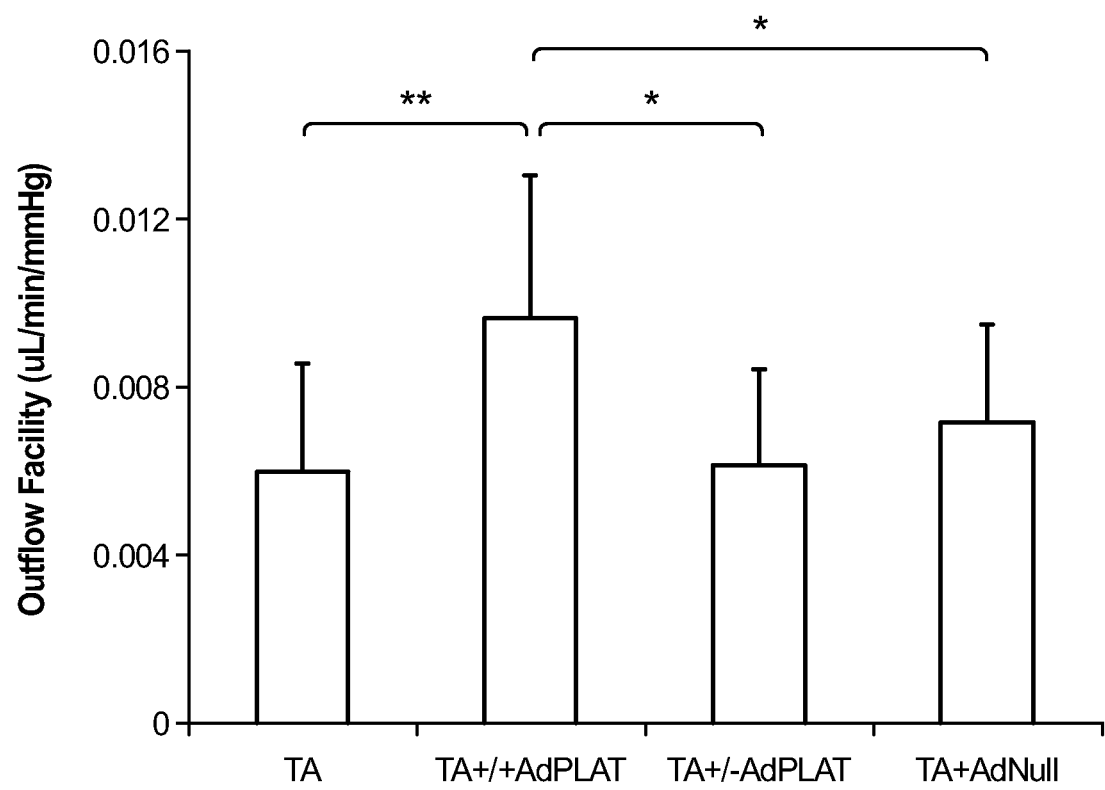
FIGS. 1A-1B. Gene therapy with Adenovirus vectors carrying transgene (AdPLAT) can prevent or reverse steroid-induced reduced outflow facility. (A), Effect of AdPLAT on outflow facility in mice treated concurrently with the steroid triamcinolone acetonide (TA). TA, average outflow facility (µl/min/mmHg) of eyes treated with triamcinolone acetonide (TA) only. TA+PLAT, average outflow facility of eyes treated with TA and transfected with AdPLAT vector, showing expression of mCherry/AdPLAT. TA+/−PLAT, average outflow facility of eyes treated with TA and transfected with AdPLAT vector, showing no or minimal expression of mCherry/AdPLAT. TA+AdNull, average outflow facility of eyes treated with TA and transfected with control vector. (B), Effect of AdPLAT on outflow facility in mice pretreated with TA. TA, average outflow facility (µl/min/mmHg) of eyes treated with triamcinolone acetonide (TA)
Figure 1B:
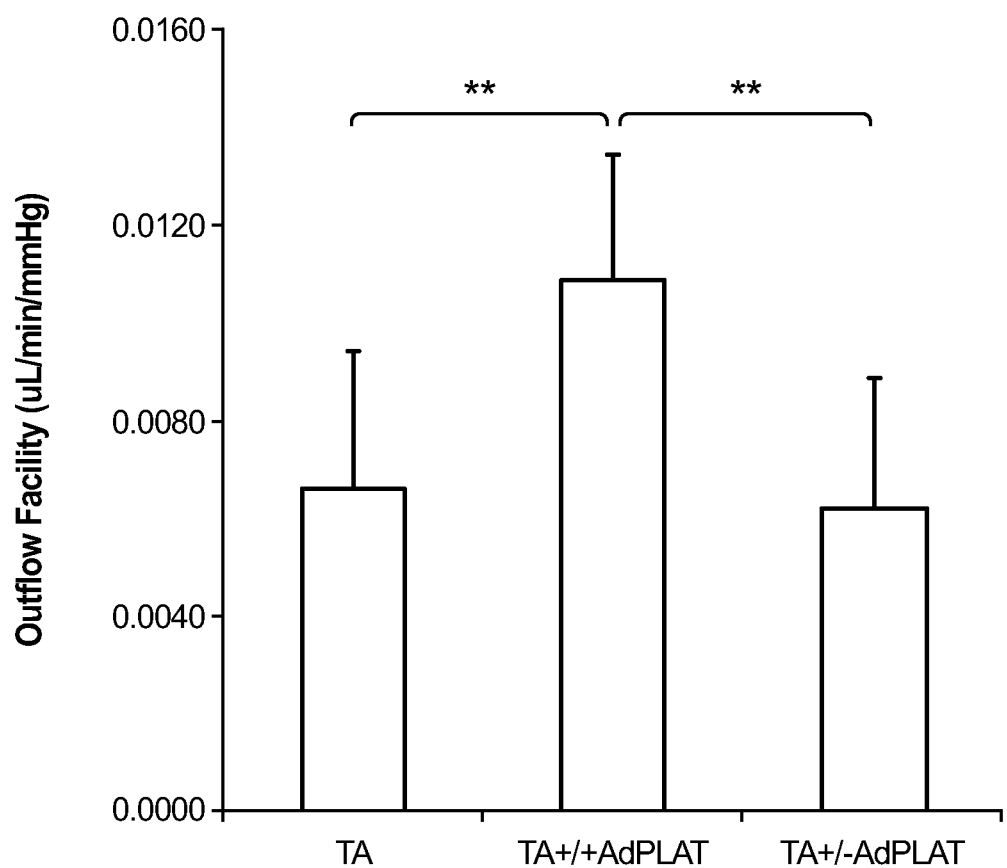

Discussion. Mice develop a steroid induced outflow facility reduction when treated with triamcinolone. The inventors used this animal model to test the effectiveness of tPA to prevent and reverse these changes. To deliver tPA in the trabecular meshwork the inventors generated an adenoviral vector (AdV) that carries the sheep tPA gene (PLAT) together with Histone2b tagged with a fluorescent protein (mCherry) under the control of CMV promoter. The inventors injected the AdV in mouse eyes either concurrently or 1 week after periocular injection of triamcinolone acetonide. Animals were sacrificed 1 week after AdV injection and outflow facility was determined. The eyes were then examined for expression of mCherry-H2B. Eyes with visible expression of mCherry (which is a surrogate for PLAT expression) showed a statistically significant (p<0.05) increase in outflow facility compared with eyes receiving a null AdV and eyes receiving the active AdV but without mCherry expression (FIG. 1A). This was true for both mice receiving the AdV concurrently as well as 1 week after triamcinolone administration (FIG. 1B). Some eyes (both with and without mCherry expression) showed mild corneal clouding.

Thus, treatment with AdPLAT can both prevent an increase in outflow facility caused by steroid treatment, as seen in FIG. 1A, and reverse a decrease in outflow facility caused by steroid treatment, as seen in FIG. 1B.

Example 2

Treatment of Mice with Small Molecules

Mice were treated by gavage with a mixture of simvastatin, curcumin and troglitazone ("SCT"). Medications were selected for their direct and indirect effects on tPA. Treatment was initiated 5 days before the administration of steroids as in 1 above and continued for the duration of the experiment. One week after steroid administration outflow facility was measured as above. As seen in FIG. 3, outflow facility of eyes treated with the small molecule combination (SCT+TA) was similar to that of control eyes (Control) and significantly higher than that of steroid treated only eyes (TA_BL). Average+SD for SCT+TA group were 0.00776667±0.00240884 µl/min/mmHg.

Thus, small molecule treatment can lower IOP and improve outflow facility.

Example 3

Treatment of Sheep with Recombinant Human tPA

Methods. The inventors used recombinant human tissue plasminogen activator (rtPA) (ACTILYSE; Boehringer Ingelheim SA, Buenos Aires, Argentina) in two different protocols.

Protocol 1. 8 sheep of the Corriedale breed were treated with prednisolone acetate three times a day in both eyes, leading to elevated IOP. After one week, the animals received intravitreal injections of human recombinant tPA (100, 200, 500 and 1000 µs, two animals each) dissolved in balanced salt solution (BSS) in one eye. IOP was monitored for 19 more days while the animals continued to receive treatment with prednisolone. Periodic slit lamp examination was also performed.

Results—Protocol 1. Sheep develop a well characterized IOP elevation after treatment with topical prednisolone acetate (Gerometta, R., et al., Invest Ophthalmol Vis Sci 50(2): 669-73 (2009)). This treatment is caused by a reduction in outflow facility. As seen in FIG. 4A, treatment with prednisolone for 10 days increased mean (±SD) IOP to 24.1(±1.6) mmHg from a baseline of 10.2 (±1.1) mmHg (p<0.00001, t-test). Treatment with tPA decreased IOP within 24 h for all doses tested to 14.1(±1.1) mmHg which was significantly lower than of the contralateral uninjected eye for all animals (p<0.00003, paired t-test). The effect was evident for all tPA doses, independent of the dose (p>0.05, ANOVA) and lasted for 19 days at which time IOP in the two eyes became similar (p>0.05). Transient injection and corneal clouding was observed in some eyes but was unrelated to the dose injected.

Protocol 2. In a second set of experiments, arginine was added to the BSS vehicle administered to the left eye to control for the relatively high concentration of the amino acid in the commercially available tPA lyophilisate. In these experiments all right eyes received 0.1 mg tPA, which concomitantly delivered 4.23 mg of arginine into the vitreous, and the left eye received this same amount of arginine, absent the tPA. On Day 1, prednisolone treatments were also begun simultaneously on both eyes.

Results—Protocol 2. Treatment with arginine alone failed to reduce outflow facility in the eye receiving arginine plus prednisolone (OS), compared to the eye treated with tPA and prednisolone (OD). See FIG. 4B.

Example 4

Treatment of Sheep with tPA Prevents IOP Elevation

Methods. In this experiment, the inventor sought to detect the effects of tPA treatment on prevention of steroid-induced IOP elevation. In 4 sheep tPA was injected in one eye (100 µs) and they were started on prednisolone acetate three times a day in both eyes. Animals were monitored for 11 days on continuous treatment.

Results. As can be seen in FIG. 4C, rtPA prevented IOP elevation in the eyes treated with steroids when administered concurrent with steroid therapy. Transient injection and corneal clouding was observed in some eyes.

Example 5 tPA Mediates Outflow Facility in the Absence of Steroid Treatment

Results. To determine whether the above findings are relevant in the regulation of outflow facility, without the exogenous administration of steroids, and thus determine the physiological significance of tPA, the inventors determined outflow facility in tPA (PLAT)-knock out (KO) mice maintained in the C57BL/6 background (obtained from Jackson Laboratory, Bar Harbour, Me.). These animals develop normally, are fertile, and have a normal life span. They show no histological abnormalities, but pulmonary clot lysis is 21% that of normal wildtype siblings. Fibrin dissolution by PLAT-deficient macrophages is unaffected. The animals also have normal eyes with no evidence of media opacification. The inventors determined outflow facility in a small number of eyes from KOs, heterozygotes and wild-type littermates. Outflow facility of tPA (PLAT)-KO animals was only ~50% of that of their wild type littermates (a statistically significant difference—ANOVA p<0.05, Tukey post hoc analysis), with heterozygotes having intermediate outflow facility values (FIG. 5).

Thus, tPA reduction reduces outflow facility, further supporting the use of tPA therapeutic agents to treat glaucoma and other IOP-related conditions.

Example 6

MMP Expression is Affected by tPA Treatment

Results. The inventors determined the effects of tPA on the expression of matrix metalloproteinases (MMPs) in both the steroid-induced mouse outflow facility (FIGS. 6A-6D) and the sheep IOP elevation (FIG. 7) models. In mouse eye angle rings treated with steroid, expression of PAI-1, MMP-2, MMP-9, and MMP-13 is low; however, expression of these genes is increased in eyes that express AdPLAT (FIGS. 6A-6D). In sheep, administration of tPA up-regulates expression of MMP1, MMP2, MMP9, and MMP13, as well as up-regulating PAI-1 expression in the trabecular meshwork (TM) and the ciliary processes (FIG. 7). These data suggest that tPA action is at least in part mediated through MMP upregulation.

Example 7

Gene Expression in Sheep Treated with tPA

Methods. Tissue Collection and Isolation of RNA. After animals were euthanized, eyes were immediately enucleated. Eyes were then opened anterior to the equator using a razor blade. The lens was removed from the anterior part, and the tissue was immersed in RNA stabilizing agent (RNAlater; Ambion, Carlsbad, Calif.) and placed at 208 C for transportation to the United States. Upon arrival in the United States, TM and ciliary processes (CP) were dissected on ice in the presence of RNA stabilizing agent as described previously. Dissected tissue was homogenized, and total RNA was extracted using TRIzol reagent (Gibco, Carlsbad, Calif.). Briefly, the tissue was homogenized in TRIzol, and chloroform was added to separate proteins from RNA. After centrifugation, the RNA-containing supernatant was aspirated. The RNA was precipitated with isopropanol, washed with 75% ethanol, treated with DNase, and column purified using a commercial kit (RNAeasy Mini Kit; Qiagen, Valencia, Calif.) in accordance with the manufacturer's instructions. RNA concentrations were determined with a spectrophotometer (Nanodrop; Thermo Scientific, Wilmington, Del.) and the 260:280-nm absorbance ratio was calculated to determine RNA purity.

Quantitative Real-Time PCR (qRT-PCR) The RNA samples were reverse transcribed with random hexamers to cDNA using a reverse transcription kit (Quantitect; Qiagen) in accordance with the manufacturer's instructions. Quantitative RT-PCR was performed using a commercial kit (SYBR Green RT-PCR Reagents Kit; Applied Biosystems, Carlsbad, Calif.) in an ABI PRISM 7900HT sequence detector (Applied Biosystems). The sheep endogenous mRNA expression of matrix metalloproteinase-1 (MMP-1), matrix metalloproteinase-2 (MMP-2), matrix metalloproteinase-9 (MMP-9), matrix metalloproteinase-13 (MMP-13), and plasminogen activator tissue (PLAT) in the TM were investigated. Plasminogen activator inhibitor 1 (PAI-1) mRNA expression was measured in both TM and ciliary processes tissues. The primer sequences used are listed in the Table. Relative quantification of gene expression was performed using the standard curve method. Mean threshold cycle (Ct) of the samples was compared among the groups by using the Ct of 18S as an internal control. The DCt was calculated as the difference in Ct values derived from the target gene and the 18S gene. The DDCt was calculated as DCt of the normalized assayed genes in the treated samples minus DCt of normalized assayed genes in the naive control samples. Relative expression was calculated by the 2exp DD Ct formula.

Results. Administration of tPA up-regulates expression of specific matrix metalloproteinases (MMPs) MMP1 and MMP9, and down-regulates PLAT expression (FIG. 7).

Example 8

PLAT is Upregulated Early After Steroid Application

Results. The probability that PLAT expression is directly modulated by steroid is supported by the fact that the PLAT gene has multiple transcription factor binding sites. Bioinformatic analysis (DECODE—SABiosciences) reveals that both the human and mouse PLAT genes have binding sites for the glucocorticoid receptors (GR) (alpha and beta), AP1, CREB and NF-KappaB (all reported to act with GR to cause gene repression) within the genomic interval of 20 kB upstream and 10 kb downstream of the gene start codon, suggesting that such direct regulation is possible. In experiments in HTM cells from two donors, the inventors detected PLAT expression downregulation as early as 1 hour after prednisolone administration (FIG. 8). Thus, steroid treatment downregulates tPA. In addition, tPA downregulation represents a biomarker for the development of steroid-induced IOP elevation.

In addition, an additional study on HTM cells indicates that steroid regulation of PLAT is dependent on the first 800 bases proximal to the ATG site of PLAT (FIG. 9).

Example 9

Administration of tPA Agents to the Anterior Chamber Reduces IOP

Methods. Lyophilized tPA, obtained as Acetilyse® from Boehringer Ingelheim S. A. (Buenos Aires) containing arginine, was used. Five sheep of the Coriedale breed were selected. Initially all eyes received instillation of 1% prednisolone 3 times/day for 10 days to elevate their IOP from 10 mm Hg to about 23 mm Hg. Then, 0.0001 µg was injected into one of the eyes and its effect was followed for up to 55:00 hrs while the instillation of prednisolone continued in both eyes. The same protocol was implemented for the 0.001 and 0.01 µg amounts (after extended washout) in the contra lateral eyes. Arginine, which is associated with 0.01 ug tPA, was injected alone and had no effect.

Results: Injection of 0.0001 µg into the AC had no effect on IOP of 23.0 mm Hg at 6:00 and 30:00 hrs after injection. 0.001 µg reduced IOP from 23.1 to 18.6 mmHg at 6:00 hr but IOP recovered to 22.3 mm Hg at 30:00 hr. Injection of 0.01 µg produced a marked and prolonged reduction of IOP. From a baseline of 23.4, IOP was reduced to 14.2, 19.0, 20.9, and 22.3 mm Hg at 6:00, 30:00, 48:00 and 55:00 hrs, respectively.

Thus, tPA is effective in reversing steroid-induced IOP elevation in sheep. The reduction of IOP elevation may be the result of an effect on extra-cellular matrix turnover in the TM. These findings further support the usefulness of tPA agents in the treatment of steroid-induced glaucoma.

What is claimed is:

1. A method of treatment for chronic elevated intraocular pressure (IOP) in a subject, the method comprising:
   administering to said subject a therapeutically effective amount of a tissue plasminogen activator (tPA) or a recombinant tPA variant for a period of at least two weeks, wherein the therapeutically effective amount of tPA or recombinant tPA variant is administered at a dosage of 10-120 µl per dose.

2. The method of claim 1, wherein the administration comprises recurrent administration of said tPA or said recombinant tPA variant.

3. The method of claim 1, wherein administration of the tPA or recombinant tPA variant reduces IOP in said subject, relative to IOP measurements in said subject prior to administration of the tPA or recombinant tPA variant, for a period of at least one day to a year.

4. The method of claim 1, wherein a second agent is administered, wherein said second agent is selected from the group consisting of: a tPA: a recombinant tPA variant: a small molecule tPA agonist; an RNA molecule that causes tPA upregulation; a polypeptide that causes tPA upregulation; an RNA molecule or other agent that down-regulates a negative regulator of tPA expression or activity; and a gene therapy vector.

5. The method of claim 4, wherein the second agent is a small molecule tPA agonist, or a functional analog of a small molecule tPA agonist, said small molecule tPA agonist being selected from the group consisting of: an oxysterol, N-acetyl-cysteine, Neovastat, nicotine, allopregnanolone, testosterone, forskolin, L-threo-DOPS, PACAP, a PDE4 activator, 5-azacytidine, CPT-cAMP, retinoic acid, a phorbol ester, 8-bromo-cAMP, 2-diocynoyl-sn-glycerol (diC8), Phorbol 12 myristate 13 acetate (PMA), AF12198, CE3F4, Prostaglandin E2 (PGE2), Butyrate, 1,25-dihydroxyvitamin D-3, estradiol, an estrogen analogue, laminin, Interleukin-6 (IL-6), ascorbic acid, sesamol, and lysophosphatidylcholine.

6. The method of claim 1, wherein said subject has glaucoma.

7. The method of claim 1, wherein the tPA or recombinant tPA variant is administered topically, systemically, by injection, by iontophoresis, or by implantation of cells that produce said tPA.

8. The method of claim 2, wherein the tPA or the recombinant tPA variant is administered to said subject for a period of at least one month.

9. The method of claim 1, wherein the subject's intraocular pressure (IOC) is reduced by between 1 mmHg and 10 mmHg.

10. The method of claim 1, wherein the subject's intraocular pressure (IOC) is reduced by between 10 mmHg and 20 mmHg.

11. The method of claim 7, wherein the injection is intracameral injection.

12. The method of claim 1, wherein 20-100 ng of the tPA or the recombinant tPA variant is administered per day.

13. The method of claim 1, wherein 40-80 ng of the tPA or the recombinant tPA variant is administered per day.

14. The method of claim 1, wherein 48-50 ng of the tPA or the recombinant tPA variant is administered per day.

15. The method of claim 1, wherein the therapeutically effective amount of the tPA or the recombinant tPA variant is in the range of 10 µg to 120 µg.

16. The method of claim 1, wherein the therapeutically effective amount of the tPA or the recombinant tPA variant is in the range of 30 µg to 100 µg.

17. The method of claim 1, wherein the therapeutically effective amount of the tPA or the recombinant tPA variant is in the range of 25 µg to 50 µg.

18. A method of treatment for a chronic elevated intraocular pressure (IOP) in a subject, comprising:
administering to said subject a therapeutically effective amount of a tissue plasminogen activator (tPA) or recombinant tPA variant for a period of at least two weeks, wherein the therapeutically effective amount is in the range of 10 µg to 120 µg.

* * * * *